(12) United States Patent
Fu et al.

(10) Patent No.: US 10,018,544 B2
(45) Date of Patent: Jul. 10, 2018

(54) ELECTROMAGNETIC MULTIAXIAL FATIGUE TESTING MACHINE

(71) Applicant: Hohai University, Nanjing, Jiangsu (CN)

(72) Inventors: Zhongqiu Fu, Jiangsu (CN); Bohai Ji, Jiangsu (CN); Faxiang Xie, Jiangsu (CN); Lin Chen, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 0 days.

(21) Appl. No.: 15/523,952

(22) PCT Filed: Sep. 21, 2015

(86) PCT No.: PCT/CN2015/090134
§ 371 (c)(1),
(2) Date: May 3, 2017

(87) PCT Pub. No.: WO2017/000395
PCT Pub. Date: Jan. 5, 2017

(65) Prior Publication Data
US 2017/0356831 A1 Dec. 14, 2017

(30) Foreign Application Priority Data
Jul. 1, 2015 (CN) .......................... 2015 1 0379770

(51) Int. Cl.
*G01N 3/20* (2006.01)

(52) U.S. Cl.
CPC ......... *G01N 3/20* (2013.01); *G01N 2203/005* (2013.01); *G01N 2203/0073* (2013.01)

(58) Field of Classification Search
CPC ............... G01N 3/20; G01N 2203/005; G01N 2203/0073
(Continued)

(56) References Cited

U.S. PATENT DOCUMENTS

| 6,718,833 B2 | 4/2004 | Xie et al. |
| 2008/0092665 A1* | 4/2008 | Melz ........................ G01N 3/38 73/841 |

(Continued)

FOREIGN PATENT DOCUMENTS

| CN | 101620043 | 1/2010 |
| CN | 203643254 | 6/2014 |

(Continued)

OTHER PUBLICATIONS

International Search Report and Written Opinion of PCT/CN2015/090134 dated Feb. 29, 2016, 12 pages (English and Chinese).

*Primary Examiner* — Max Noori
(74) *Attorney, Agent, or Firm* — Rankin, Hill & Clark LLP

(57) ABSTRACT

An electromagnetic multiaxial fatigue testing machine includes a test piece fixing platform and an electromagnet loading mechanism arranged on a frame, wherein the electromagnet loading mechanism includes a first loading device for bend loading, and a second loading device for axial and torsional loading. The first loading device includes a first permanent magnet and a first electromagnet with a direction of a magnetic force generated therebetween is orthogonal to an axial direction of a test piece; the second loading device includes a second permanent magnet and a second electromagnet mounted on a swinging pair with a direction of a magnetic force generated therebetween is parallel to the axial direction of the test piece.

17 Claims, 6 Drawing Sheets

(58) Field of Classification Search
USPC .......................................................... 73/849
See application file for complete search history.

(56) References Cited

U.S. PATENT DOCUMENTS

2015/0300936 A1* 10/2015 Edward .............. G01N 33/2847
324/629
2016/0228180 A1* 8/2016 Sliwa ................... A61B 5/6885

FOREIGN PATENT DOCUMENTS

| CN | 103900916 | 7/2014 |
| CN | 104132857 | 11/2014 |
| CN | 104990820 | 10/2015 |
| JP | 5225949 | 2/2011 |

* cited by examiner

ELECTROMAGNETIC MULTIAXIAL FATIGUE TESTING MACHINE

TECHNICAL FIELD

The present invention relates to an instrument for testing strength characteristics of a solid material via a mechanical stress, and more particularly, to an electromagnetic multiaxial fatigue testing machine, which belongs to the field of structure test.

BACKGROUND

Fatigue failure is one of the most important failure modes of engineering structures, which threatens the safety and causes huge economic losses. Therefore, various countries in the world attach great importance to researches in the field of fatigue fracture. A lot of scholars at home and abroad have made a great deal of researches on the theory of uniaxial fatigue, and accumulated rich experience and valuable data. However, there are few researches on the multiaxial fatigue of building structures in China. Some special or new structural details in the steel bridge structures, such as a cable-girder anchorage zone of a cable-stayed bridge, an orthotropic steel bridge deck, an integral joint and a pipe structure welding node and the like, show stronger multi-axis effect in fatigue behavior. Therefore, the research of multiaxial fatigue is closer to engineering practice than uniaxial fatigue.

For the research of structure fatigue under a constant amplitude loading action, an S-N curve of the material can be used to estimate the number of cycles experienced to damage at different stress levels. However, for cyclic loading at two or more stress levels, it is not possible to estimate the service life directly using the S-N curve, and the fatigue cumulative damage criterion needs to be used as well. The researches on cumulative fatigue damage have been lasted for decades, but a satisfactory uniform model has not been made so far. Moreover, the actual structure is often in a complex state of stress, so that a lot of experiments are also required to research the structure fatigue damage rules.

At present, the research on structure fatigue tests is mainly based on uniaxial fatigue tests; while the multiaxial tests still depend on large-scale loading equipment such as MTS and the like, so that the test has low efficiency and is uneconomical. Through searching, China patent document CN103994936A discloses a horizontal high-tonnage energy-saving fatigue experiment device which is applied to the field of mechanical design and metal material performance testing. The horizontal high-tonnage energy-saving fatigue experiment device includes a shell, an actuating cylinder, an actuating cylinder piston rod, actuating cylinder oil inlet and outlet pipelines, hydraulic servo flow valves, a first energy accumulating device, a second energy accumulating device and an electromagnet loading device; wherein the electromagnet loading device comprises a soft magnet, an electric magnet, a load sensor, an electromagnet loading actuating rod and an electromagnet controller. The electromagnet loading device is combined with a traditional dual-output-rod high-tonnage fatigue testing machine. The electromagnet loading starts until the existing high-tonnage actuating cylinder is loaded to an average load as required for test, for saving the energy sources as required for the actuating cylinder to keep pressure, the actuating cylinder is also required while starting, and limits to the uniaxial fatigue test.

Based on the above circumstances, designing a novel economic multiaxial fatigue testing machine capable of simulating actual structure loading becomes an urgent technical problem to be solved.

BRIEF DESCRIPTION

Object of the invention: in order to overcome the defects in the prior art, the present invention provides a multifunctional electromagnetic multiaxial fatigue testing machine, which adopts an electromagnet principle for loading, and does not cause mechanical frictions, so that the testing efficiency is improved, and the testing noise and testing cost are reduced.

Technical solutions: in order to solve the technical problems above, the present invention provides an electromagnetic multiaxial fatigue testing machine, which includes a test piece fixing platform and a loading mechanism arranged on a frame, wherein the loading mechanism is an electromagnet loading mechanism, the electromagnet loading mechanism includes a first loading device for bend loading, and a second loading device for axial and torsional loading.

To be specific, the first loading device includes a first permanent magnet and a first electromagnet, and a direction of a magnetic force generated between the first permanent magnet and the first electromagnet is orthogonal to an axial direction of a test piece.

To be specific, the first permanent magnet is mounted on the test piece, and the first electromagnet is mounted on the frame.

To be specific, the first permanent magnet is mounted on the frame, and the first electromagnet is mounted on the test piece.

To be specific, the second loading device includes a second permanent magnet and a second electromagnet mounted on a swinging pair, a direction of a magnetic force generated between the second permanent magnet and the second electromagnet is parallel to the axial direction of the test piece, the swinging pair includes a driving swinging beam, a driven swinging beam and a movement, the driven swinging beam is clamped on the test piece, and the driving swinging beam is in transmission connection with the movement.

To be specific, the second permanent magnet is mounted on the driven swinging beam and a movement, the second electromagnet is mounted on the driving swinging beam, the second permanent magnet is a pair of permanent magnets mounted by taking the axis of the test piece as a symmetric center, and the second electromagnet is a pair of electromagnets mounted by taking the axis of test piece as a symmetric center.

To be specific, the second permanent magnet is mounted on the driven swinging beam, and the second electromagnet is mounted on the driving swinging beam.

To be specific, the movement comprises a variable frequency motor, a pair of cams mounted at two ends of an output shaft of the variable frequency motor, and a set of transmission rods matched with the cams, and the transmission rods are connected with the driven swinging beam.

To be specific, the movement is mounted on a lifting device, the driving swinging beam and the driven swinging beam are provided with a chute for regulating a position of the first permanent magnet or the second electromagnet, and the chute is provided with a scale.

To be specific, the frame is provided with a rail for regulating a distance between the loading mechanism and the test piece, the frame is provided with a rail for regulating a height of the movement, and the frame is provided with a movement locking disc for fixing the movement.

The frame mainly includes the test piece fixing platform, a movable frame, a movable base and a testing machine base. The first electromagnet is mounted on an electromagnet base and the electromagnet base is connected with the movable base. The first electromagnet is moved up and down by a base locking switch and is moved and fixed in a first electromagnet moving chute in the testing machine base, so as to adapt to the requirements of test pieces with different sizes. The second electromagnet is mounted on the driving swinging beam, and the driving swinging beam is driven by the movement.

The movement mainly includes a variable frequency motor, a first cam, a second cam, a swinging shaft, a main swinging rod, an auxiliary swinging rod, a first horizontal transmission rod, a second horizontal transmission rod, an auxiliary positioning shaft, vertical transmission rods and a roller. The main swinging rod, the auxiliary swinging rod and a pair of vertical transmission rods form a parallel four-link mechanism. The first cam and the second cam are mounted at two sides of the variable frequency motor respectively in a reverse direction. One ends of the swinging shaft, the first horizontal transmission rod and the second horizontal transmission rod are fixed with the driving swinging beam respectively, while the other end of the swinging shaft is fixed with the main swinging rod, and the other ends of the first horizontal transmission rod and the second horizontal transmission rod are hinged with the main swinging rod. One end of the auxiliary positioning shaft is fixed on a movement shell, while the other end thereof is hinged with the auxiliary swinging rod. The vertical transmission rod is hinged with the main swinging rod and the auxiliary swinging rod respectively. The roller is mounted at a bottom end of the vertical transmission rod, and is contacted with the first cam and the second cam respectively. When the testing machine works, the variable frequency motor rotates to drive the first cam and the second cam to rotate. A power is transmitted by the first cam and the second cam mounted in a reverse direction to the vertical transmission rod via the roller, the power staggered up and down is transmitted by the vertical transmission rod to the first horizontal transmission rod and the second horizontal transmission rod respectively, and the driving swinging beam is finally driven by the first horizontal transmission rod and the second horizontal transmission rod to repeatedly swing in a fixed-axis around the swinging shaft.

The movement is mounted in the movable frame, and the movement is moved up and down through a movement lifting rail under a function of a jack, so that the second electromagnet can adapt to the heights as required for different types of fatigue test pieces. When reaching the testing height as required, the movement is locked at the height through the movement locking disc, thereby ensuring that the testing machine is kept stable in the working process.

During testing, the test piece is mounted on the test piece fixing platform, the driven swinging beam is mounted at an end portion of the test piece, a lower portion of the driven swinging beam is equipped with the first permanent magnet, and a front portion is equipped with the second permanent magnet. The movable base is regulated so that the first electromagnet is at an appropriate height below the first permanent magnet, and the first electromagnet is positioned and locked through the base locking switch. Meanwhile, the height of the movement is regulated, so that the first electromagnet and the second permanent magnet are located at the same horizontal position. The movable frame is moved through the frame rail, so that a horizontal space between the second electromagnet and the second permanent magnet is appropriate; therefore, the movable frame can be fixed finally.

The principle of the electromagnetic multiaxial fatigue testing machine is as follows:

1. The first electromagnet generates magnetic forces in different directions and sizes by controlling a current magnitude, a current direction and a changing speed of the current direction to form a variable amplitude, variable frequency attraction force or repulsive force to the first permanent magnet, and thus making the test piece clamped by the driven swinging beam generate a bend cyclic loading effect;

2. The second electromagnet generates magnetic forces in different sizes by controlling the current magnitude and a changing speed of the current magnitude to form a pulsed attraction force to the second permanent magnet, and thus making the test piece produce an axial cyclic loading effect.

3. When the second electromagnet applies an axial magnetic load to the test piece, the driving swinging beam swings in a reciprocating manner, and a torsional cyclic loading effect is generated to the test piece through the attraction force of the second electromagnet to the permanent magnet. Meanwhile, the second electromagnet and the second permanent magnet can be moved and regulated on the driving swinging beam and the driven swing beam in a left-right direction respectively, and a torsional moment and a torsional amplitude are changed by changing an arm of force. A scale label is engraved in the beam, which can conveniently regulate a length of the arm of force.

Advantageous effects: an electromagnet principle is adopted in the invention for loading, which does not cause mechanical frictions, so that the testing efficiency is improved, and the testing noise and testing cost are reduced. Moreover, a uniaxial loading mode can be implemented when using the three loading modes separately, and a multiaxial loading mode can be implemented when the three loading modes are combined to use. During a fatigue test, the loading mode is selected according to the working principle of the fatigue testing machine and the loading type as required for the fatigue test piece. To be specific, various multiaxial loading modes as follows can be implemented: 1) bending and axial biaxial loading; 2) bending and torsional biaxial loading; 3) axial and torsional biaxial loading; and 4) simultaneous bending, axial and torsional triaxial loading. In addition, the present invention can also perform bending, axial and torsional uniaxial loading according to the test requirements.

In addition to the above technical problems solved by the invention, the technical features forming the technical solutions and the advantages brought about by the technical features of the technical solutions, other technical problems that can be solved by the electromagnetic multiaxial fatigue testing machine according to the invention, other technical features included in the technical solutions and advantages brought about by these technical features will be further described in details with reference to the drawings.

In the figures: 1 refers to test piece fixing platform; 2 refers to movable frame; 3 refers to testing machine base; 4 refers to frame rail; 5 refers to a first electromagnet moving chute; 6 refers to first electromagnet; 7 refers to second electromagnet; 8 refers to driving swinging beam; 9 refers to electromagnet base; 10 refers to movable base; 11 refers to base locking switch; 12 refers to movement locking disc; 13 refers to driven swinging beam; 14 refers to clamping slice; 15 refers to first permanent magnet; 16 refers to second permanent magnet; 17 refers to movement; 18 refers to jack; 19 refers to movement lifting rail; 20 refers to frame fixing bolt; 21 refers to driven swinging beam fixing bolt; 22 refers to test piece fixing bolt; 23 refers to faceplate hole; 24 refers to backplate hole; 25 refers to main swinging rod; 25 refers to auxiliary swinging rod; 27 refers to vertical transmission rod; 28 refers to roller; 29 refers to swinging shaft; 30 refers to auxiliary positioning shaft; 31*a* refers to first horizontal transmission rod; 31*b* refers to second horizontal transmission rod; 32 variable frequency motor; 33*a* refers to first cam; 33*b* refers to second cam; 34 refers to transmission rod hole; 35 refers to movement lifting rail groove; 36 refers to transmission shaft hole; 37 refers to auxiliary positioning shaft fixing position; 38 refers to variable frequency motor fixing position; and 39 refers to test piece.

DETAILED DESCRIPTION

Embodiment

The present invention will be further illustrated with reference to the drawings and the specific embodiments. It should be understood that these embodiments are used for describing the present invention merely, but are not intended to limit the scope of the present invention. Various equivalent modifications made to the present invention by those skilled in the art after reading the present invention shall all fall within the scope limited by the claims.

Figure 1:
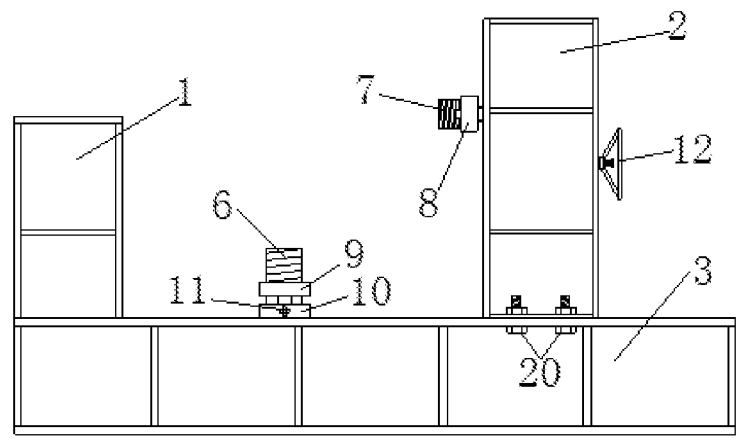
FIG. 1 is a front view of an electromagnetic multiaxial fatigue testing machine in the embodiment of the present invention.
Figure 2:
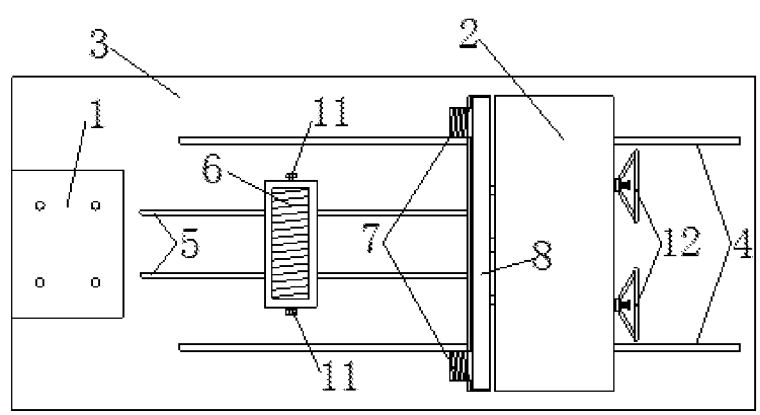
FIG. 2 is a top view of FIG. 1.

As shown in FIG. 1 and FIG. 2, a testing machine mainly includes a test piece fixing platform 1, a movable frame 2, a testing machine base 3, a first electromagnet 6, a second electromagnet 7, a first permanent magnet 15, a second permanent magnet 16, a driving swinging beam 8, a driven swinging beam 13 and a movement 17, wherein the first electromagnet is mounted on an electromagnet base 9 and the electromagnet base 9 is connected with the movable base 10, the first electromagnet is moved up and down by a base locking switch 11 and is moved and fixed in a first electromagnet moving chute 5 in the testing machine base, so as to adapt to the requirements of test pieces with different sizes. The second electromagnet is mounted on the driving swinging beam, and the driving swinging beam is driven by the movement.

Figure 3:
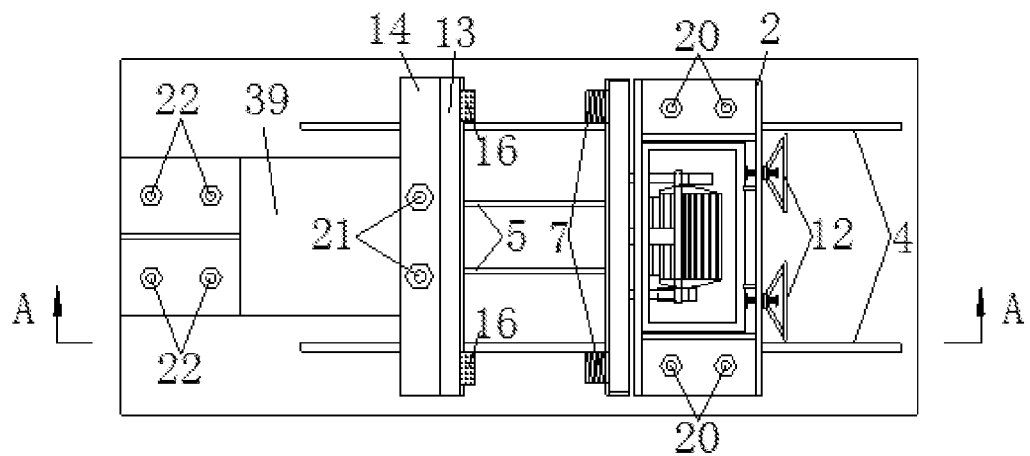
FIG. 3 is a schematic diagram of FIG. 2 after mounting a test piece.
Figure 4:
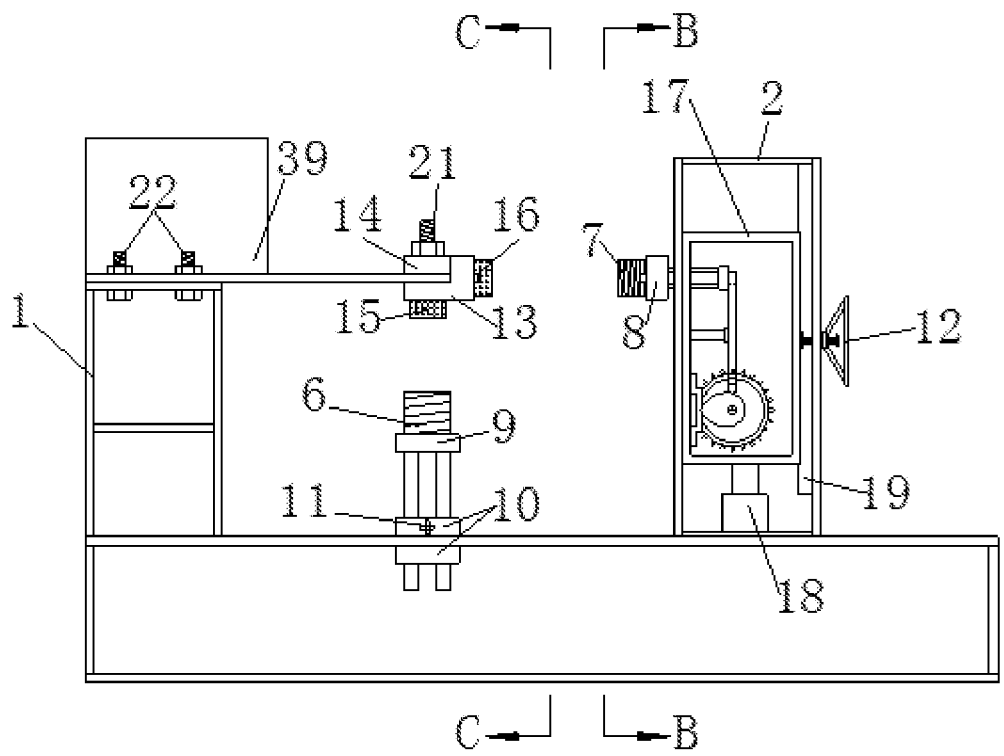
FIG. 4 is an A-A section view of FIG. 3.

As shown in FIG. 3 and FIG. 4, during testing, a test piece in a certain fatigable portion of a steel bridge is used as a test piece 39, and is mounted on the test piece fixing platform through a test piece fixing bolt 22, the driven swinging beam 13 is mounted at an end portion of the test piece through a driven swinging beam fixing bolt 21 and a clamping slice 14, a lower portion of the driven swinging beam is equipped with the first permanent magnet 15, and the front portion is equipped with the second permanent magnet 16. The movable base is regulated, so that the first electromagnet 6 is at an appropriate height below the first permanent magnet 15, and the first electromagnet 6 is positioned and locked through the base locking switch. Meanwhile, the height of the movement is regulated, so that the first electromagnet 7 and the second permanent magnet 16 are located at the same horizontal position. The movable frame 2 is moved through the frame rail 4, so that a horizontal space between the second electromagnet 7 and the second permanent magnet 16 is appropriate; therefore, the movable frame 2 can be fixed through a frame fixing bolt 20 finally.

As shown in FIG. 4, the movement is mounted in the movable frame, the movement is moved up and down through a movement lifting rail 19 under a function of a jack 18, so that the second electromagnet can adapt to the heights as required for different types of fatigue test pieces. When reaching the testing height as required, the movement is locked at the height through the movement locking disc 12, thereby ensuring that the testing machine is kept stable in the working process.

Figure 5:
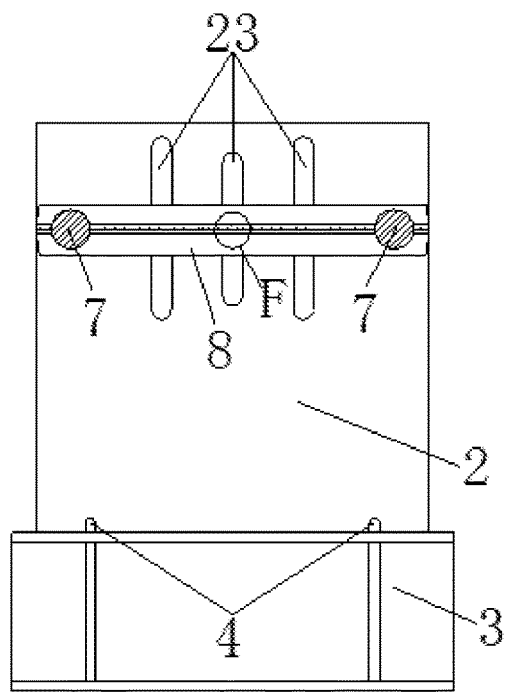
FIG. 5 is a B-B section view of FIG. 4.
Figure 6:
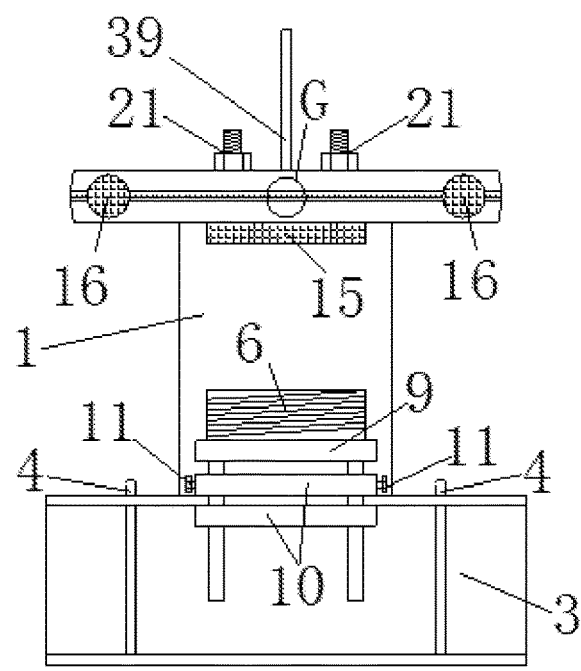
FIG. 6 is a C-C section view of FIG. 4.

As shown in FIG. 5 and FIG. 6, when the fatigue testing machine performs torsional loading, the second electromagnet and the second permanent magnet can be moved and regulated on the driving swinging beam and the driven swing beam in a left-right direction respectively, and a torsional moment and a torsional amplitude are changed by changing an arm of force. A scale label is engraved in the beam, which can conveniently regulate a length of the arm of form.

Figure 7:
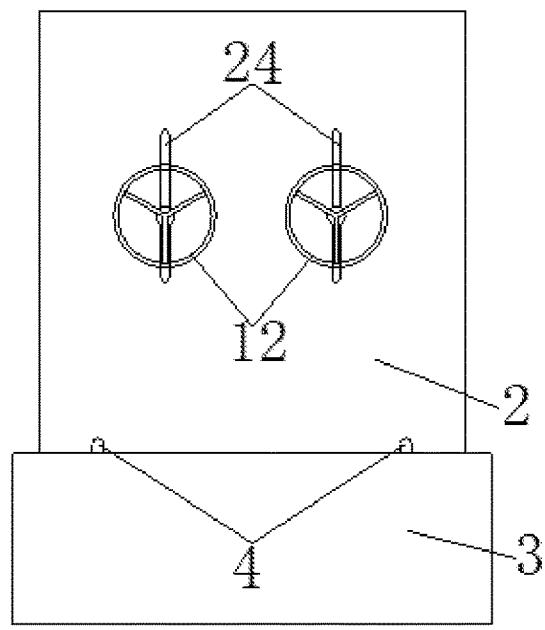
FIG. 7 is a right view of FIG. 4.
Figure 12:
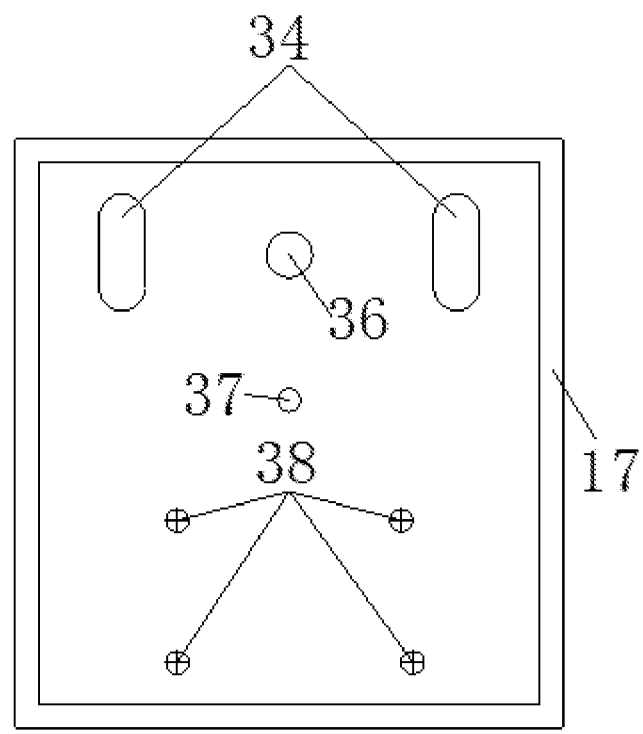
FIG. 12 is a structural schematic diagram of a movement shell in FIG. 9.

As shown in FIG. 5, FIG. 7 and FIG. 12, a faceplate hole 33 and a backplate hole 24 are arranged in the movable frame in order to facilitate moving up and down the movement, a transmission rod hole 34 is arranged in the movement shell in order to facilitate swinging the first horizontal transmission rod and the horizontal transmission rod, and a transmission shaft hole 36, an auxiliary positioning shaft fixing position 37 and a variable frequency motor fixing position 38 are arranged in the movement shell at the same time in order to meet the construction requirements.

Figure 8:
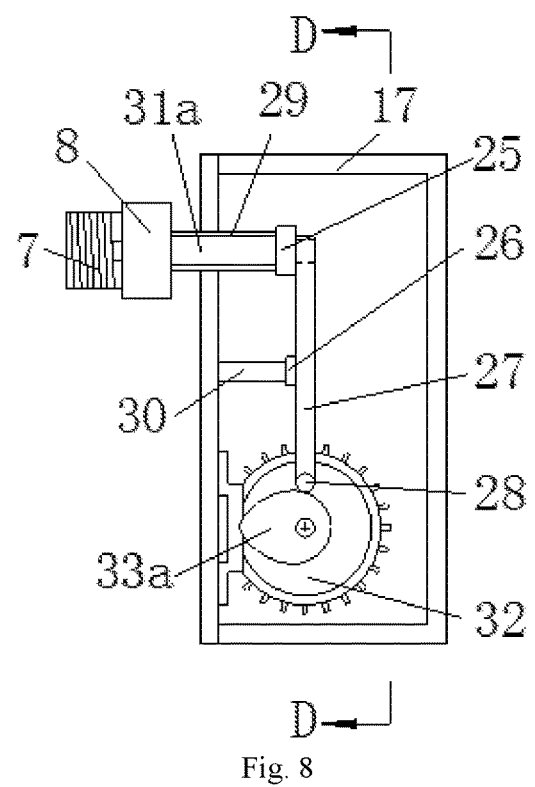
FIG. 8 is a structural schematic diagram of a movement in FIG. 4.
Figure 9:
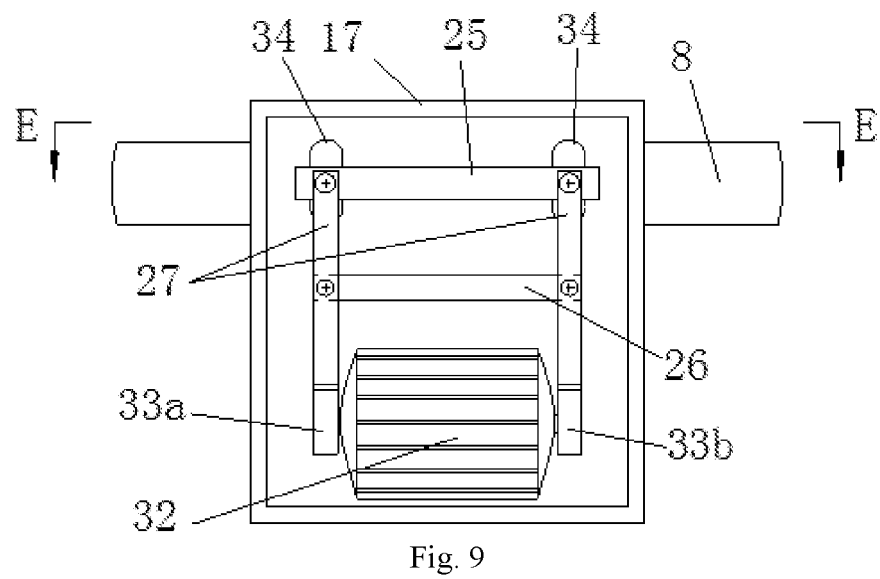
FIG. 9 is a D-D section view of FIG. 8.
Figure 10:
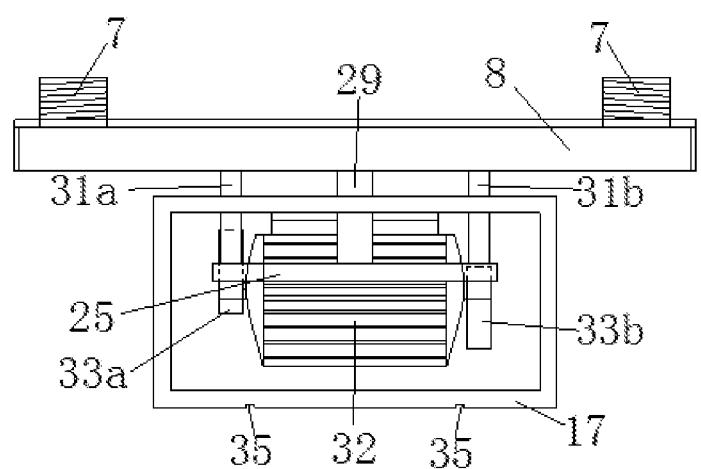
FIG. 10 is an E-E section view of FIG. 9.

As shown in FIG. 8, FIG. 9 and FIG. 10, the movement mainly includes a variable frequency motor 32, a first cam 33*a*, a second cam 33*b*, a swinging shaft 29, a driving swinging rod 25, an auxiliary swinging rod 26, a first horizontal transmission rod 31*a*, a second horizontal transmission rod 31*b*, an auxiliary positioning shaft 30, a vertical transmission rod 27 and a roller 28. The first cam and the second cam are mounted at two sides of the variable frequency motor respectively in a reverse direction. One ends of the swinging shaft, the first horizontal transmission rod and the second horizontal transmission rod are fixed with the driving swinging beam respectively, while the other end of the swinging shaft is fixed with the main swinging rod, and the other ends of the first horizontal transmission rod and the second horizontal transmission rod are hinged with the main swinging rod. One end of the auxiliary positioning shaft is fixed on movement shell, while the other end thereof is hinged with the auxiliary swinging rod. The vertical transmission rod is hinged with the main swinging rod and the auxiliary swinging rod respectively. The roller is mounted at a bottom end of the vertical transmission rod, and is contacted with the first cam and the second cam respectively.

Figure 11:
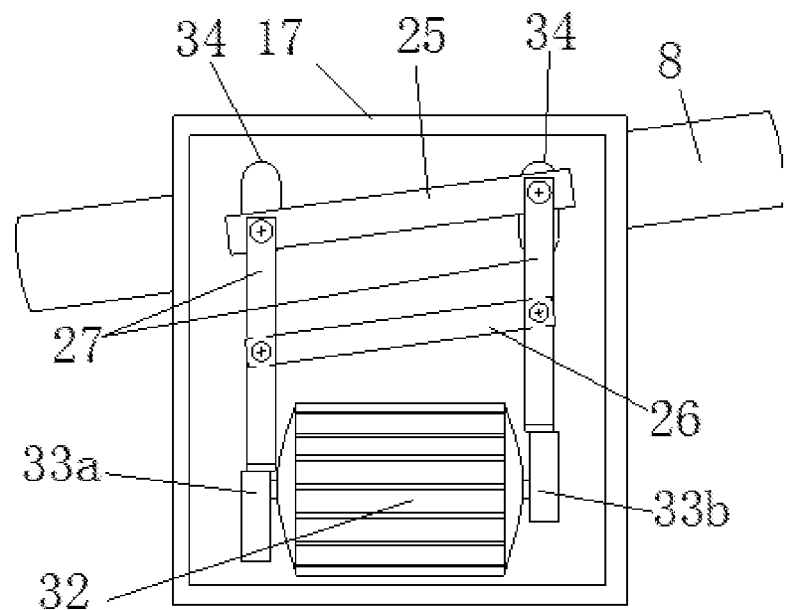
FIG. 11 is a schematic diagram of a working state of FIG. 9.

As shown in FIG. 11, when the testing machine works, the variable frequency motor rotates to drive the first cam and the second cam to rotate. A power is transmitted by the first cam and the second cam arranged in a reverse direction to the vertical transmission rod through the roller, the power staggered up and down is transmitted by the vertical transmission rod to the first horizontal transmission rod and the second horizontal transmission rod respectively, and the driving swinging beam is finally driven by the first horizontal transmission rod and the second horizontal transmission rod to repeatedly swing in a fixed-axis around the swinging shaft.

During the fatigue test, the loading mode is selected according to the working principle of the fatigue testing machine and the loading type as required for the fatigue test piece. To be specific, various multiaxial loading modes as follows can be implemented: 1) bending and axial biaxial loading; 2) bending and torsional biaxial loading; 3) axial and torsional biaxial loading; and 4) simultaneous bending, axial and torsional triaxial loading. In addition, the present invention can also perform bending, axial and torsional uniaxial loading according to the test requirements.

The principle of the electromagnetic multiaxial fatigue testing machine is as follows: 1. the first electromagnet 6 generates magnetic forces in different directions and sizes by controlling a changing speed of the current magnitude, the current direction and the current direction to form a variable amplitude, variable frequency attraction force or repulsive force to the first permanent magnet 15, and thus making the test piece clamped by the driven swinging beam generate a bend cyclic loading effect; 2. the second electromagnet 7 generates magnetic forces in different sizes by controlling a current magnitude and a changing speed of the current magnitude to form a pulsed attraction force to the second permanent magnet 16, and thus making the test piece produce an axial cyclic loading effect; and 3. when the second electromagnet applies the axial magnetic load to the test piece, the driving swinging beam 8 swings in a reciprocating manner, and a torsional cyclic loading effect is generated to the test piece through the attraction force of the second electromagnet to the permanent magnet. Moreover, a uniaxial loading mode can be implemented when the three loading modes are used separately, and a multiaxial loading mode can be implemented when the three loading modes are combined to use.

The embodiments of the invention are described in details hereinabove with reference to the drawings, but the invention is not limited to the described embodiments. Various changes, modifications, replacements and transformations made to these embodiments by those having ordinary skills in the art, within the scope of the principle and technical ideas of the invention shall still fall within the protection scope of the invention.

The invention claimed is:

1. An electromagnetic multiaxial fatigue testing machine, comprising a test piece fixing platform and a loading mechanism arranged on a frame, wherein the loading mechanism is an electromagnet loading mechanism, the electromagnet loading mechanism comprises a first loading device for bend loading, and a second loading device for axial and torsional loading, wherein the second loading device comprises a second permanent magnet and a second electromagnet mounted on a swinging pair, a direction of a magnetic force generated between the second permanent magnet and the second electromagnet is parallel to the axial direction of the test piece, the swinging pair comprises a driving swinging beam, a driven swinging beam and a movement, the driven swinging beam is clamped on the test piece through a clamping slice, and the driving swinging beam is in transmission connection with the movement.

2. The electromagnetic multiaxial fatigue testing machine according to claim 1, wherein the first loading device comprises a first permanent magnet and a first electromagnet, and a direction of a magnetic force generated between the first permanent magnet and the first electromagnet is orthogonal to an axial direction of a test piece.

3. The electromagnetic multiaxial fatigue testing machine according to claim 2, wherein the first permanent magnet is mounted on the test piece and the first electromagnet is mounted on the frame.

4. The electromagnetic multiaxial fatigue testing machine according to claim 2, wherein the first permanent magnet is mounted on the frame and the first electromagnet is mounted on the test piece.

5. The electromagnetic multiaxial fatigue testing machine according to claim 1, wherein the second permanent magnet is mounted on the driven swinging beam, the second electromagnet is mounted on the driving swinging beam, the second permanent magnet is a pair of permanent magnets mounted by taking the axis of the test piece as a symmetric center, and the second electromagnet is a pair of electromagnets mounted by taking the axis of test piece as a symmetric center.

6. The electromagnetic multiaxial fatigue testing machine according to claim 1, wherein the second permanent magnet is mounted on the driving swinging beam, and the second electromagnet is mounted on the driven swinging beam.

7. The electromagnetic multiaxial fatigue testing machine according to claim 1, wherein the movement comprises a variable frequency motor, a pair of cams mounted at two ends of an output shaft of the variable frequency motor, and a set of transmission rods matched with the cams, and the transmission rods are connected with the driven swinging beam.

8. The electromagnetic multiaxial fatigue testing machine according to claim 1, wherein the movement is mounted on a lifting device, the driving swinging beam and the driven swinging beam are provided with a chute for regulating a position of the first permanent magnet or the second electromagnet, and the chute is provided with a scale.

9. The electromagnetic multiaxial fatigue testing machine according to claim 1, wherein the frame is provided with a rail for regulating a distance between the loading mechanism and the test piece, the frame is provided with a rail for regulating a height of the movement, and the frame is provided with a movement locking disc for fixing the movement.

10. The electromagnetic multiaxial fatigue testing machine according to claim 2, wherein the frame is provided with a rail for regulating a distance between the loading mechanism and the test piece, the frame is provided with a rail for regulating a height of the movement, and the frame is provided with a movement locking disc for fixing the movement.

11. The electromagnetic multiaxial fatigue testing machine according to claim 3, wherein the frame is provided with a rail for regulating a distance between the loading mechanism and the test piece, the frame is provided with a rail for regulating a height of the movement, and the frame is provided with a movement locking disc for fixing the movement.

12. The electromagnetic multiaxial fatigue testing machine according to claim 4, wherein the frame is provided with a rail for regulating a distance between the loading mechanism and the test piece, the frame is provided with a rail for regulating a height of the movement, and the frame is provided with a movement locking disc for fixing the movement.

13. The electromagnetic multiaxial fatigue testing machine according to claim 1, wherein the frame is provided with a rail for regulating a distance between the loading mechanism and the test piece, the frame is provided with a rail for regulating a height of the movement, and the frame is provided with a movement locking disc for fixing the movement.

14. The electromagnetic multiaxial fatigue testing machine according to claim 2, wherein the frame is provided with a rail for regulating a distance between the loading mechanism and the test piece, the frame is provided with a rail for regulating a height of the movement, and the frame is provided with a movement locking disc for fixing the movement.

15. The electromagnetic multiaxial fatigue testing machine according to claim 5, wherein the frame is provided with a rail for regulating a distance between the loading mechanism and the test piece, the frame is provided with a rail for regulating a height of the movement, and the frame is provided with a movement locking disc for fixing the movement.

16. The electromagnetic multiaxial fatigue testing machine according to claim 6, wherein the frame is provided with a rail for regulating a distance between the loading mechanism and the test piece, the frame is provided with a rail for regulating a height of the movement, and the frame is provided with a movement locking disc for fixing the movement.

17. The electromagnetic multiaxial fatigue testing machine according to claim 7, wherein the frame is provided with a rail for regulating a distance between the loading mechanism and the test piece, the frame is provided with a rail for regulating a height of the movement, and the frame is provided with a movement locking disc for fixing the movement.

* * * * *